United States Patent [19]
Kim et al.

[11] Patent Number: 5,500,007
[45] Date of Patent: Mar. 19, 1996

[54] THERAPEUTIC, PORTABLE WATER BED ASSEMBLY HAVING A WATER HEATING SYSTEM

[76] Inventors: Yong H. Kim; Soon J. Kim, both of 1309 Ruppert Rd., Silver Spring, Md. 20903

[21] Appl. No.: 257,284

[22] Filed: Jun. 9, 1994

[51] Int. Cl.⁶ .............................. A47C 21/00; A61F 7/00
[52] U.S. Cl. .................. 607/104; 607/96; 5/421
[58] Field of Search .............. 607/96, 104, 108–112, 607/114; 5/421–422, 284, 8

[56] References Cited

U.S. PATENT DOCUMENTS

| | | |
|---|---|---|
| 17,102 | 4/1857 | Lefebvre . |
| 825,763 | 7/1906 | Schaefer . |
| 1,121,277 | 12/1914 | Mitchell . |
| 1,817,277 | 8/1931 | Uhlig . |
| 4,114,620 | 9/1978 | Moore et al. . |
| 4,149,541 | 4/1979 | Gammons et al. . |
| 4,561,441 | 12/1985 | Kolodziej . |
| 4,884,304 | 12/1989 | Elkins . |
| 5,146,633 | 9/1992 | Kim et al. . |
| 5,241,959 | 9/1993 | Kim et al. ...................... 607/96 X |
| 5,259,379 | 11/1993 | Kim et al. . |

Primary Examiner—Angela D. Sykes
Attorney, Agent, or Firm—Birch, Stewart, Kolasch & Birch

[57] ABSTRACT

A therapeutic, portable water heating bed assembly having a pair of beds, includes a water heater attached to and disposed within a base member of the bed, a water pillow which functions as a water tank, a straight water pipe extending through a concrete plate of the base member independently, a power control switch connected to the water heater, and a laminated paper on the concrete plate, whereby the bed assembly can be easily moved, the water pillow can maintain cold water, and the laminated paper and the cool water pillow can warm and treat a human body lying on the beds.

8 Claims, 2 Drawing Sheets

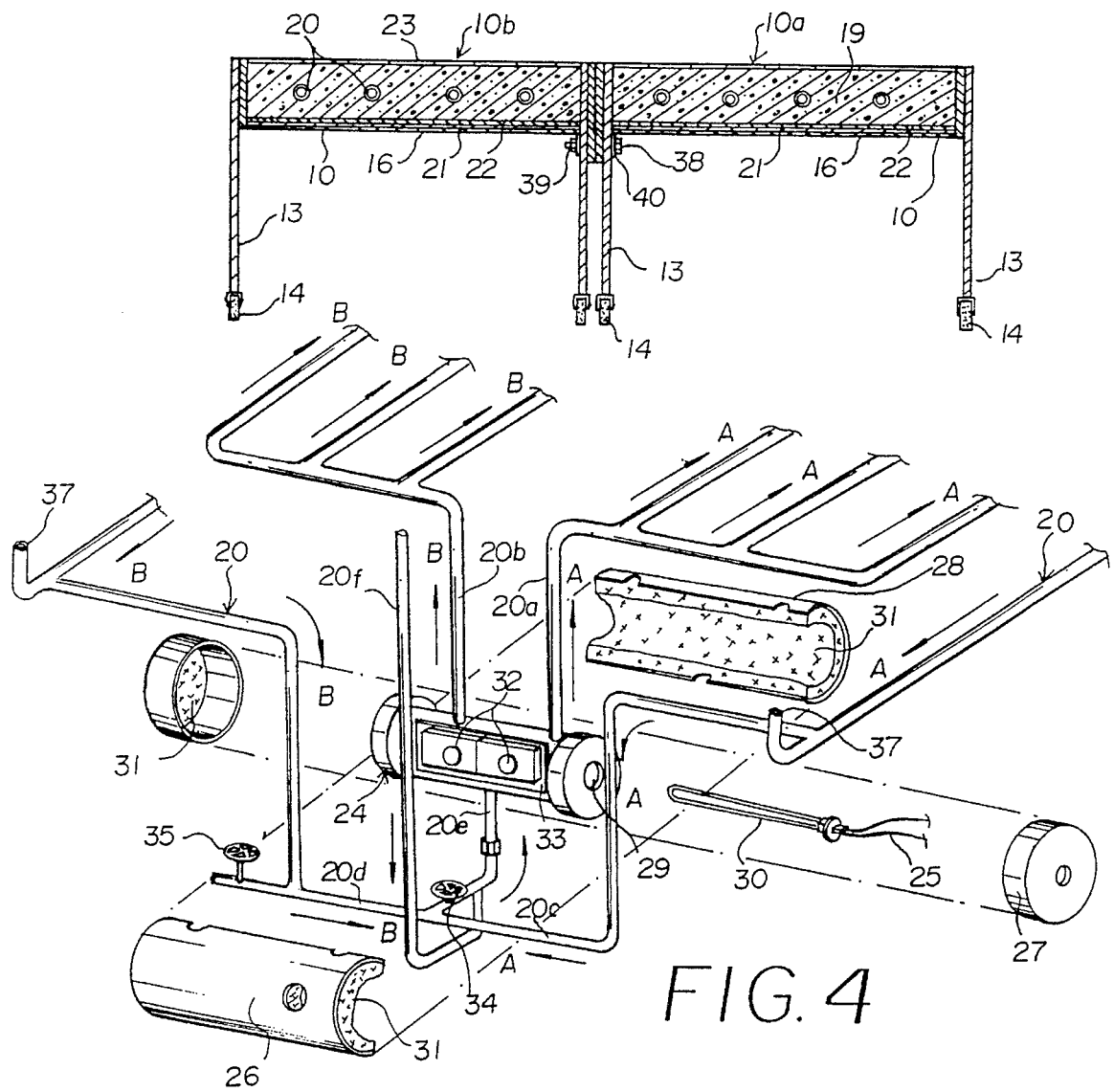
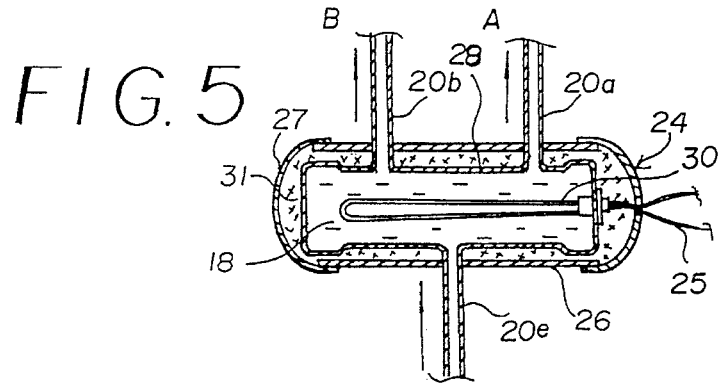

THERAPEUTIC, PORTABLE WATER BED ASSEMBLY HAVING A WATER HEATING SYSTEM

BACKGROUND OF THE INVENTION

1. Field of the Invention

The present invention relates to a therapeutic, portable water heating bed assembly provided with a heating system and more particularly, to a portable water heating bed including a pair of beds for assembling with and disassembling from each other, which includes each bed having a base member, a serpentine configured water pipe extending through the base member, and a water heater, whereby the portable water heating bed assembly can warm a person lying on a pad on the bed by circulating hot water in the water pipe through the water heater attached to the base member.

2. Description of the Related Art

Various types of water heating beds are well known in the art. Such prior art water heating beds include a separate water heating system and a fixed base bed communicating with the water heating system through a water pipe as shown in U.S. Pat. Nos. 17,102 to Lefebure, 825,763 to Schafer, 1,121,277 to Mitchell, and 1,817,277 to Uhlig.

Also, various types of water heating pads are well known in the art. Such prior art water heating pads include a water pipe disposed therein and a separate or composite electric heater for heating the water disposed in the pad as shown in U.S. Pat. Nos. 4,114,620 to Moore et al., 4,149,541 to Gammons et al., 4,561,441 to Kolodziej, and 4,884,304 to Elkins.

However, such prior art devices suffer from a number of problems such as, for example, (a) it is very difficult to move the bed with the heating system, (b) it is complicated in structure such as a separate water tank, a separate heater, etc., (c) it is not expected to achieve a treatment effect for the human body, and (d) it is inconvenient to move due to a separate water heater from the bed compared with a bed having a water heater of the present invention.

In order to avoid the above described problems, U.S. Pat. No. 5,146,633, issued to the present inventors, discloses a therapeutic, portable bed including an electric water heating system attached to and disposed within a base member of the bed, a hollow headboard of the bed, which functions as a water tank, a serpentine configured water pipe extending through a concrete plate of the base member, and a cotton pad member containing mugwort herb, disposed on a laminated paper cover on the concrete plate, whereby the bed can be easily moved and a vapor from the cotton pad can warm and treat the human body lying on the bed.

Another U.S. Pat. No. 5,259,379 issued to the present inventors, discloses a therapeutic, portable folding chair provided with a heating system, which includes a base member, a serpentine configured water pipe, a hollow top portion of the back which functions as a water tank, a water heater attached to and disposed within the base member, and a mugwort herb pad disposed on the base member, whereby the folding chair can be easily moved and a vapor generated from the pad heated by the water pipe through the water heater warms and treats the human body sitting thereon or lying on a bed converted from the folding chair.

A further U.S. patent issued to the present inventor discloses a therapeutic, portable bed assembly having a pair of beds, includes an electric water heating system disposed within a base member of the bed, a U-shaped tube disposed on a circumferential edge of the bed which functions as a water tank, a serpentine configured water pipe extending through a concrete plate of the base member, and a pad member containing mugwort herb disposed on a laminated paper cover on the concrete plate, whereby the bed can be easily moved and a vapor from the cotton pad can warm and treat the human body lying on the bed. However, these therapeutic portable beds have some disadvantages such as, for example, it is complicated to have a water tank in a headboard and a chair back, and it is difficult to transport since these beds are heavy. Although such beds include a pair of beds, the serpentine water pipe extends through both beds, so that it is difficult to assemble and disassemble from each other, and it is possible to leak water from jointed water pipes. Furthermore, there is no water pillow and power control switch.

SUMMARY OF THE INVENTION

Accordingly, it is an object of the present invention to provide an improved therapeutic, portable water heating bed for warming a person lying on the bed, which eliminates the above problems encountered with conventional heating beds.

Another object of the present invention is to provide a portable water heating bed assembly including a pair of beds for assembling with and disassembling from each other, which includes each bed having a base member, a water pipe extending through the base member independently, a water pillow including cold water which functions as a water tank, a laminated paper plate on a concrete plate of the base member, a power control switch, and a water heater attached to and disposed within the base member, whereby when a plug of the water heater is connected to a power source, the hot water is easily circulated within the water pipe and treats a desired region of the human body lying on the bed.

A further object of the present invention is to provide a portable water heating bed which is simple in construction, compact for portability, inexpensive to manufacture, durable in use, and refined in appearance.

Still another object of the present invention is to provide a portable water heating bed which includes a straight water pipe disposed on each bed separately for effectively accelerating water circulation within the water pipe and retaining cold water in the water pillow.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention is directed to a therapeutic, portable water heating bed assembly having a pair of beds, includes a water heater attached to and disposed within a base member of the bed, a water pillow which functions as a water tank, a straight water pipe extending through a concrete plate of the base member independently, a power control switch connected to the water heater, and a laminated paper plate on the concrete plate, whereby the bed assembly can be easily moved, the water pillow can maintain cold water, and the laminated paper plate and the cool water pillow can warm and treat the human body lying on the beds.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 3 is a sectional view of FIG. 1 taken along line 3—3;

FIG. 4 is an exploded perspective view of a water heater of the water heating bed according to the present invention; and FIG. 5 is a sectional view of the assembled water heater of FIG. 4.

DESCRIPTION OF THE PREFERRED EMBODIMENTS

Figure 1:
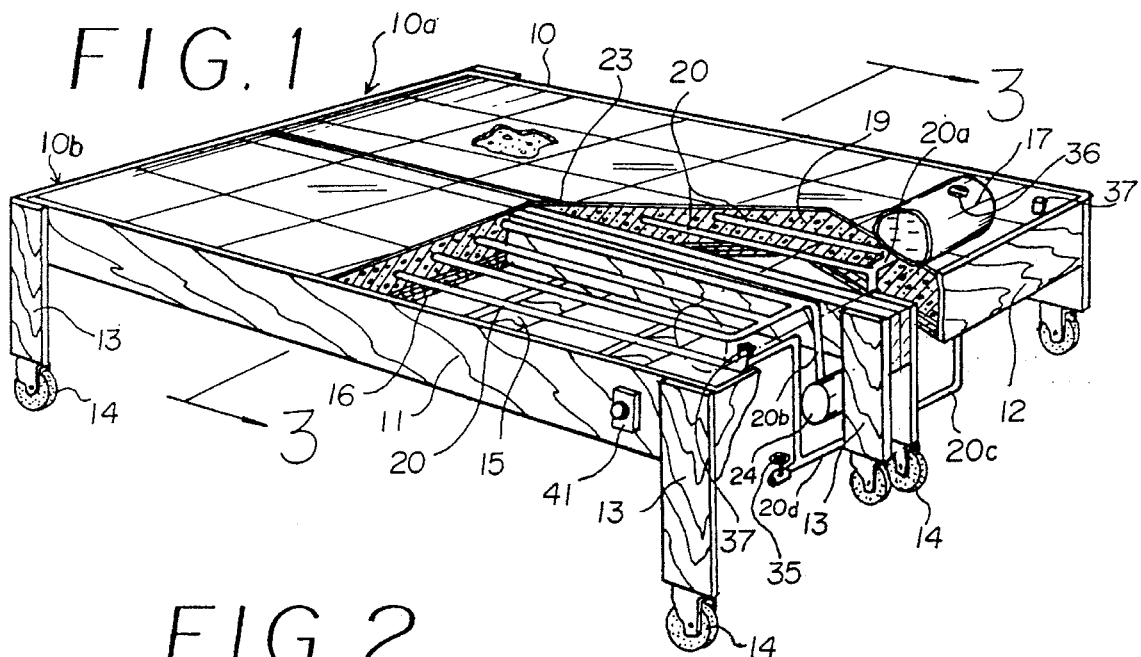
FIG. 1 is a perspective view of the therapeutic, portable water heating bed containing cut-away portions in order to illustrate the construction of the water heating bed assembly according to the present invention.
Figure 2:
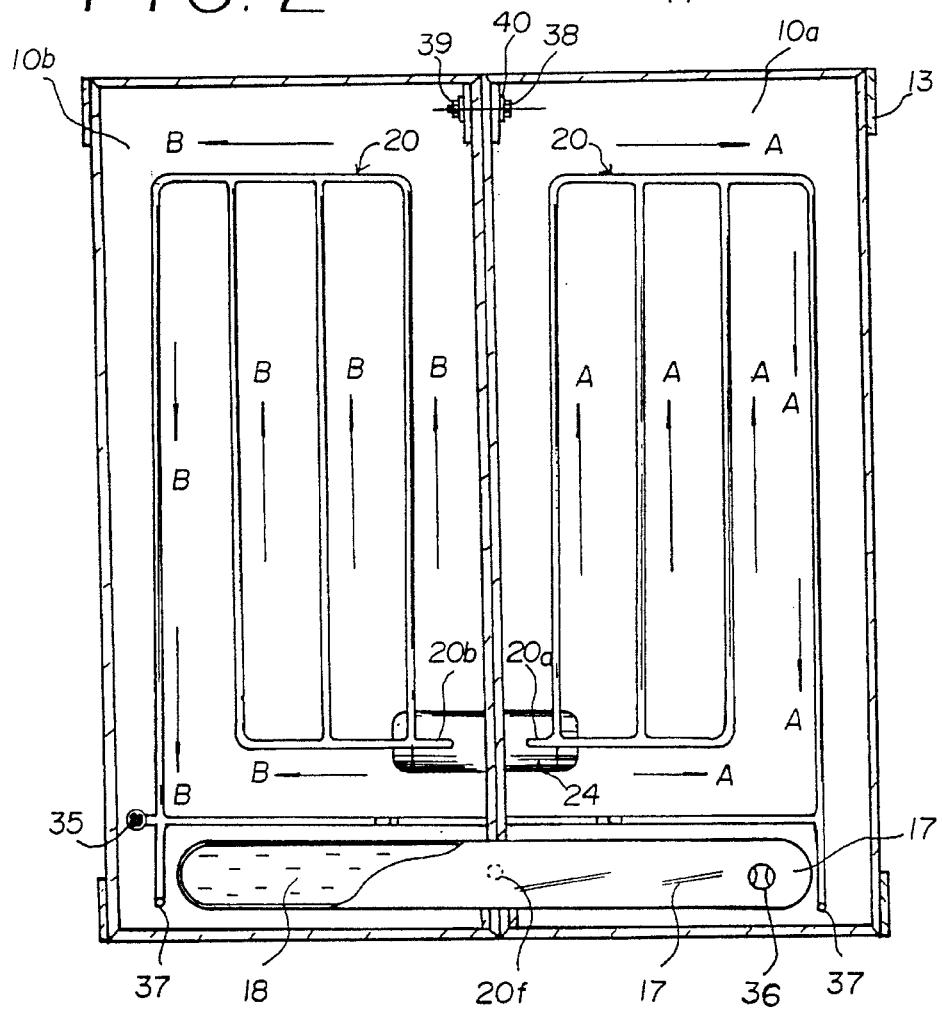
FIG. 2 is a top plan view of a water pipe extending through a base member of a bed of the water heating bed assembly of the present invention.

Referring now in detail to the drawings for the purpose of illustrating the preferred embodiment of the present invention, the therapeutic, portable water heating bed assembly provided with a water heating system as shown in FIGS. 1, 2, and 3, comprises a pair of bed members 10a and 10b for assembling with and disassembling from each other, a water pillow 17 which functions as a water tank, and an electric water heater member 24. The pair of bed members 10a and 10b include a pair of bolts, nuts, and washers for assembling with and disassembling from the pair of bed members 10a and 10b.

Each of the pair of bed members 10a and 10b includes a base bed member having a pair of longitudinal and transverse frames 11 and 12, a plurality of legs 13 with each roller 14, and a plurality of supports 15, a straight configured water pipe 20 extending through the base bed member 10a or 10b.

As shown in FIGS. 1 and 3, the base bed member 10 includes a bottom supporting wood plate 16 which is stacked on the plurality of supports an insulating plate 21 made of Styrofoam® stacked on the wood plate 16 and a wire net 22 stacked on the insulating plate 21. Thereafter, the straight configured water pipes 20 is put on the wire net 22 and then the concrete 19 is put on them for burying the water pipes 20. The concrete 19 can be reinforced by conventional concrete reinforcement. A laminated paper 23 is attached on the top of a concrete floor 19. At that time, a separate cotton pad or other pad can be covered on the laminated paper floor 23, whereby the bed can warm and treat the human body lying on the laminated paper floor 23 of the bed.

As shown in FIGS. 2 and 3, a pair of upper water outlets 20a and 20b communicated with the electric water heater member 24 communicated with the water pipes 20 disposed in the bed members 10a and 10b, respectively and a pair of lower water inlets 20c and 20d are communicated with the water pipes 20 disposed in the bed members 10a and 10b. The lower water inlets 20c and 20d are combined to become a heater water inlet 20e. A water tank outlet 20f is communicated with the heater inlet 20e.

A pair of air valves 37 are communicated with ends of water pipes 20 disposed in bed members 10a and 10b for taking air out of the pipes 20. A first switch valve 34 is located between a crossing area of the lower water inlets 20c and 20d, and the heater water inlet 20e for circulating water in an open position and changing water in a closed position. A second switch valve 35 is located on the end of the lower water inlet 20d for circulating water in a closed position and changing water in an open position.

As shown in FIGS. 4 and 5, the electric water heater member 24 includes a cylindrical heater body 28 containing water 18, the pair of upper water outlets 20a and 20b, the heater water inlet 20e, a pair of thermostats 32 mounted on a steel plate 33, and a central hole 29 for slidably receiving an electric heater 30 with a pair of electric wires 25 which is connected to a power control switch 41 disposed on the longitudinal frame 11 and near the water pillow 17. The water heater 24 is covered by a pair of semi-body covers 26 and a pair of caps 27 with each insulation material 31 disposed therein.

As shown in FIGS. 1 and 2, the water pillow 17 which functions as a water tank and communicates with the water pipes 20 and a security valve 36 disposed on the top thereof for using as a water supply inlet. The water pillow 17 retains cool water 18. The cool water 18 is introduced into the water pillow 17 by security valve 36. If the user wants to use a coolest pillow, ice water can be introduced into the water pillow 17 by the security valve 36.

The therapeutic, portable water heating bed assembly according to the present invention includes a plurality of legs 13 with a roller 14 for easy portability.

According to the present invention, the therapeutic water heating bed assembly operates as follows:

Prior to using this bed assembly, the water pillow 17 is filled with cool water 18 as shown in FIG. 1. When a plug (not shown) is connected to a power source, the concrete plate 19 and the laminated paper floor 23 are heated through the serpentine and straight water pipes 20 extending through the concrete plate 19 of the bed base member 12. The heat energy and pressure from the laminated paper floor 23 simultaneously act to treat the effected portion of the human body lying on the beds 10a and 10b.

When the pair of beds 10a and 10b are assembled with each other, the pair of bolts 38, nuts 39, and washers 40 are utilized to affix one bed 10a to the other bed 10b. At this time, accordingly, they do not need water pipe connectors and water tube connectors when compared with U.S. Pat. No. 5,241,959 issued to the present inventors.

Accordingly, when the warm water circulation is performed by being in an ON-position of the first switch valve 34 and an OFF-position of the second switch valve 35, the warm water circulation in the direction indicated by arrows (A) and (B), respectively as shown in FIGS. 2 and 4. Specifically, the water pipes 20 are in a straight configured form so that the warm water circulation accelerates and reduces air in the water pipes in comparison to those of the serpentine configured water pipes of U.S. Pat. No. 5,241,959.

If necessary, for example, if the bed assembly according to the present invention is disassembled from the pair of beds and is going to be transported, or if the old water is to be changed by fresh water, first of all, the first switch valve 34 is an OFF-position and the second switch valve 35 is an ON-position.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A therapeutic, portable water heating bed assembly provided with a water heating system, comprising:

at least one bed including, a bed base member having a bottom support member, an insulating plate, a concrete plate and a laminated paper disposed in sequence on said bottom support member, a pair of longitudinal frames, and a plurality of transverse frames, said longitudinal frames and said transverse frames defining a bed support for said insulating plate, concrete plate and laminated paper, a straight configured water pipe extending through said concrete plate of the bed base member;

a water pillow which functions as a water tank, said water pillow disposed on said laminated paper and at one end portion of said bed assembly;

a water heater member attached to said base member of the bed assembly, said water heater member communicating with said straight configured water pipes, said water heater member including, a heater body adapted to contain water and for slidably receiving a heater therewithin, and a water heater cover for covering the heater body therewithin, and at least one thermostat attached to said heater body;

connecting means for assembling said bed, whereby the bed assembly can be easily assembled and heating energy and pressure can warm and treat a human body lying above the laminated paper of the water heating bed assembly.

2. The therapeutic, portable water heating bed assembly of claim 1, wherein said straight configured water pipe is buried in said concrete plate and disposed on said wire net.

3. The therapeutic, portable water heating bed assembly of claim 1, wherein said at least one bed includes a pair of beds and said straight configured pipes of the pair of beds extend from a pair of upper outlet pipes which are communicated with said water heater member and extend to a pair of lower inlet pipes which are communicated with said water heater member through a heater inlet pipe, respectively.

4. The therapeutic, portable water heating bed assembly of claim 3, wherein said heater inlet pipe and one of said pair of lower inlet pipes are provided with a first switch valve and second switch valve, respectively for closing and opening thereof.

5. The therapeutic, portable water heating bed assembly of claim 1, wherein said water heater cover of the water heater member includes an insulation material disposed therein.

6. The therapeutic, portable water heating bed assembly of claim 1, wherein said water heater member is provided with a power control switch for controlling power to said heater member, said water power control switch attached on one wall of said longitudinal frames and near said water pillow.

7. The therapeutic, portable water heating bed assembly of claim 1, wherein said water pillow includes a security valve disposed on a top thereof.

8. The therapeutic, portable water heating bed assembly of claim 1, wherein said connecting means are bolts, nuts, and washers.

* * * * *